United States Patent
Moore

(10) Patent No.: US 6,683,935 B2
(45) Date of Patent: Jan. 27, 2004

(54) COMPUTED TOMOGRAPHY WITH VIRTUAL TILT AND ANGULATION

(75) Inventor: John F. Moore, Libertyville, IL (US)

(73) Assignee: Bio-Imaging Research, Inc., Lincolnshire, IL (US)

( * ) Notice: Subject to any disclaimer, the term of this patent is extended or adjusted under 35 U.S.C. 154(b) by 183 days.

(21) Appl. No.: 09/966,165

(22) Filed: Sep. 28, 2001

(65) Prior Publication Data

US 2003/0063703 A1 Apr. 3, 2003

(51) Int. Cl.[7] ................................................. A61B 6/00
(52) U.S. Cl. ....................................................... 378/17
(58) Field of Search ............................... 378/4, 17, 20, 378/26, 196, 197

(56) References Cited

U.S. PATENT DOCUMENTS

| | | | |
|---|---|---|---|
| 3,488,495 A | | 1/1970 | Schneeman |
| 3,984,696 A | | 10/1976 | Collica et al. |
| 4,464,775 A | * | 8/1984 | Yamagishi ..................... 378/5 |
| 4,581,538 A | | 4/1986 | Lenhart |
| 4,598,369 A | * | 7/1986 | Wang et al. ................... 378/22 |
| 4,651,007 A | * | 3/1987 | Perusek et al. ......... 250/363.08 |
| D323,386 S | | 1/1992 | Perusek |
| 5,420,427 A | | 5/1995 | Morgan et al. |
| 5,533,089 A | | 7/1996 | Mulhern |
| 6,009,147 A | | 12/1999 | Stein et al. |
| 6,217,214 B1 | * | 4/2001 | Cabral et al. ................ 378/196 |

\* cited by examiner

Primary Examiner—Max Noori
(74) Attorney, Agent, or Firm—Welsh & Katz, Ltd.

(57) ABSTRACT

A method and apparatus are provided for performing computed tomography. The method includes the steps of moving one of an X-ray source and an X-ray detector parallel to a head-to-feet axis of a prone patient and collecting data from the X-ray detector as the one of the X-ray source and X-ray detector moves along the head-to-feet axis of the prone patient.

32 Claims, 8 Drawing Sheets

ROTATION AT 0°

X-RAY SOURCE STARTS AT FAR POINT

DETECTOR STARTS AT NEAR POINT AT FRONT

ROTATION AT 90°

DETECTOR AT MIDPOINT

X-RAY SOURCE AT MIDPOINT

CT++ VIRTUAL TILT
(RANGE: ±20°)

CT++ VIRTUAL TILT
(RANGE: ±20°)

0°  X-RAY SOURCE AT MIDPOINT OF TRAVEL

DETECTOR AT MIDPOINT OF TRAVEL

90°

X-RAY AT FAR POINT OF TRAVEL

DETECTOR AT NEAR POINT AT FRONT

CT++ VIRTUAL ANGULATION
(RANGE: ±20°)

CT++ VIRTUAL ANGULATION
(RANGE: ±20°)

COMPUTED TOMOGRAPHY WITH VIRTUAL TILT AND ANGULATION

FIELD OF THE INVENTION

The field of the invention relates to computed tomography and more particularly to methods of obtaining image data from X-rays passing through a body of a prone patient at oblique angles.

BACKGROUND OF THE INVENTION

X-ray devices used for imaging and/or therapy are known. In the case of imaging, such devices are typically arranged to provide an x-ray source and detector on opposite sides of a body of a patient. The source and detector rotate in unison around the patient collecting x-ray data at discrete locations.

The x-ray source is often structured to allow X-rays to propagate through the body of the patient in the form of a fan beam. The detectors of a fan-beam device typically include an array of many individual detector elements, often arranged in the form of an arc, to detect x-rays along the spread of the fan beam.

Alternatively, the x-ray source may generate a cone beam of X-rays. The cone beam may be detected by a two-dimensional array of detectors, typically referred to as an area detector.

In operation, the source and detectors are rotated continuously around the patient, and the signals from the detectors are sampled at intervals of a few milliseconds, so that sets of x-ray absorption profiles are collected at many angular increments around the patient.

From the x-ray data, an associated computer may solve a matrix of equations, or use some other mathematical technique to obtain a measure of the x-ray absorption of each of a number of two-dimensional areas (or "pixels") within a finite thickness of the slice. The pixels may be combined to form a two-dimensional image of a cross-sectional view, or slice, through the patient's body.

After each revolution, the patient may be moved a small distance in a direction normal to the plane of the slice, and the process of x-ray exposure, data collection, and computer data reduction may be repeated to obtain an image of an adjacent slice. The motion and process may be repeated any number of times. Alternatively, the patient may be moved continuously, so that the x-ray beam follows a helical path along the body. In devices employing a cone beam, several slices may be generated simultaneously.

By correlating the data among adjacent cross-sectional slices, a three-dimensional array of data may be obtained. From the three-dimensional array of data, three-dimensional images (or two-dimensional images at orientations different from the slices) can be created, which may be used to determine the location of tumors or other lesions.

In conventional X-ray CT machines, it is not always possible to direct the X-ray source or position the X-ray detector to optimize the collection of X-ray images. As a consequence, patients must often be arranged in uncomfortable positions to facilitate the collection of X-ray data. Because of the importance of CT, a need exists for a method of collecting X-ray data that is less dependent upon the position of the patient.

SUMMARY OF THE INVENTION

A method and apparatus are provided for performing computed tomography. The method includes the steps of moving one of an X-ray source and an X-ray detector parallel to a head-to-feet axis of a prone patient and collecting data from the X-ray detector as the one of the X-ray source and X-ray detector moves along the head-to-feet axis of the prone patient.

DETAILED DESCRIPTION OF A PREFERRED EMBODIMENT

Figure 1:
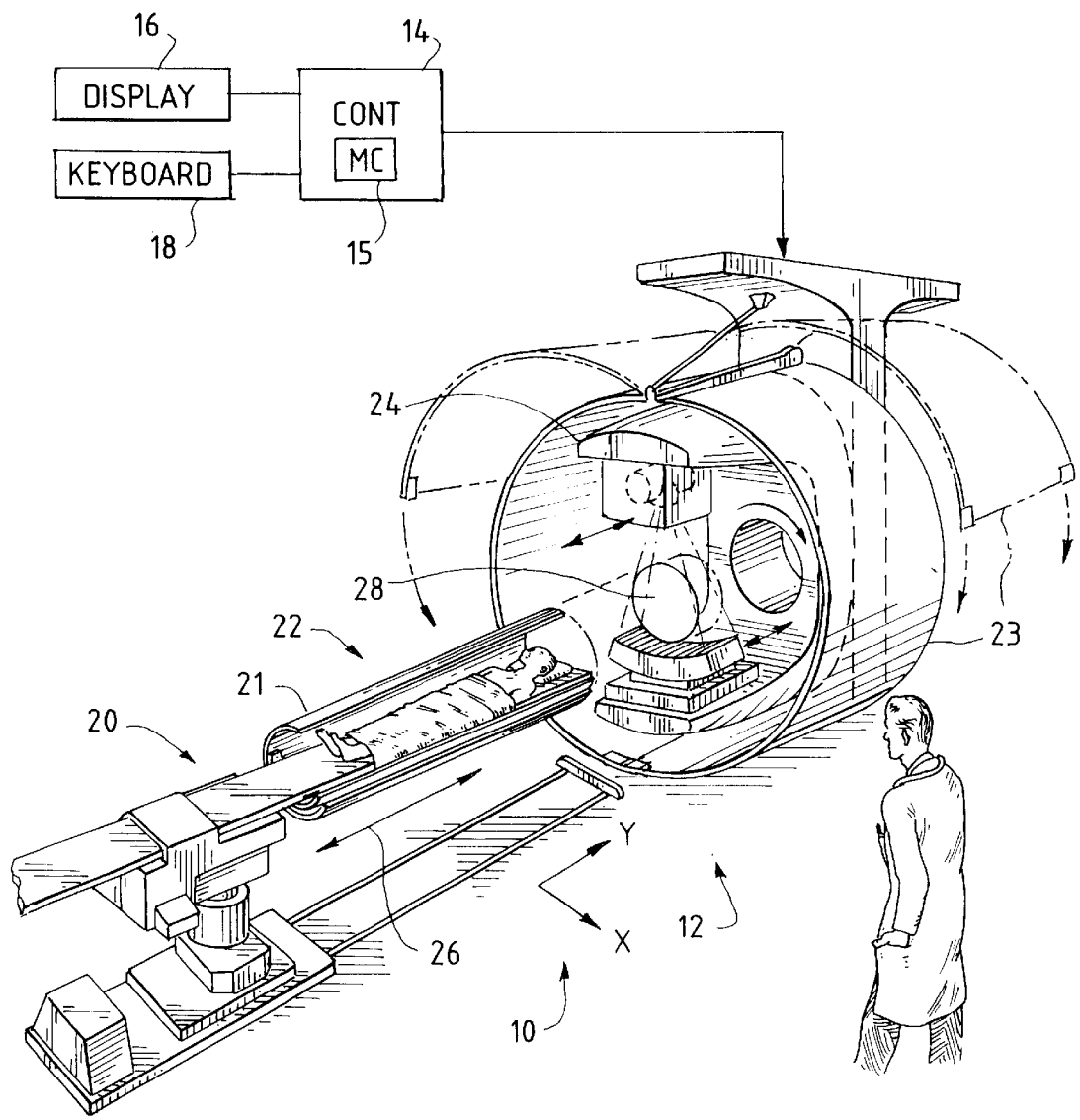
FIG. 1 is a computed tomography imaging system in accordance with an illustrated embodiment of the invention.

FIG. 1 is a perspective view of a computed tomography (CT) system 10 having virtual tilt and angulation under an illustrated embodiment of the invention. Included within the CT system 10 may be a rotatable scanner (e.g., a gantry) 12, controller 14 and a patient transport table 20.

In operation, a patient 22 may be placed on the transport table 20. The transport table 20 may be moved 26 through a scanning zone 28 either manually or under control of a transport motor (not shown).

A technician may enter one or more program identifiers into the controller 14 using a keyboard 18 and display 16. Alternatively, the technician may create a scanning program tailored to the specific needs of the patient. Once a program has been identified or entered into the controller, 14, the technician may activate the system and the system 10 may automatically collect X-ray data.

Figure 2:
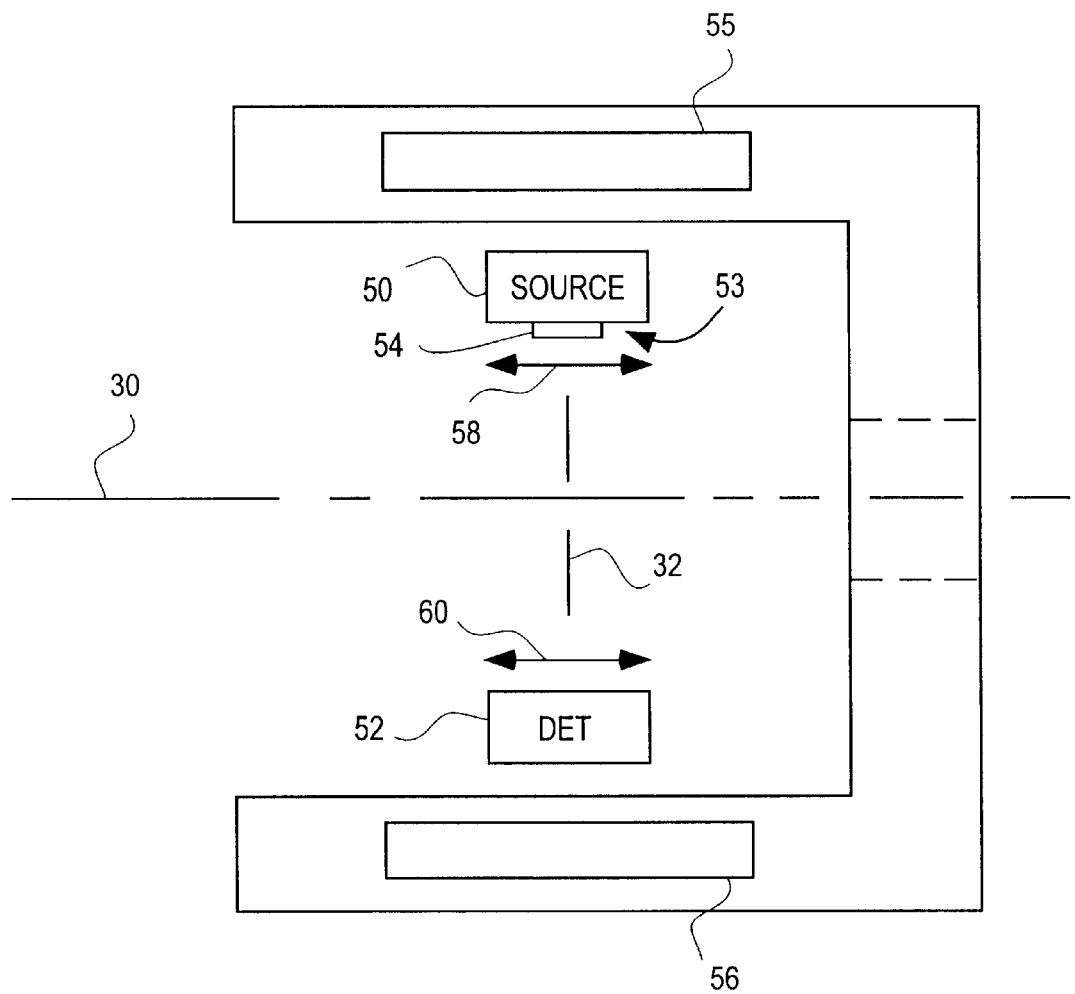
FIG. 2 is a side view of a scanner gantry of the system of FIG. 1.

The collection of X-ray data may be accomplished by operation of the scanner 24 disposed around the scanning zone 28. FIG. 2 depicts a side view of the scanner 24. The scanner 24 may be adapted to rotate around an axis 30 that also forms the center of rotation of the scanning zone 28 shown in FIG. 1. In most cases, the center of rotation of the scanning zone 28 would also be coextensive with a centerline axis of the patient 22 passing through the head and feet of the patient.

Included within the scanner 24 may be an X-ray source 50 and an X-ray detector 52. The source 50 may be conventional, except for the addition of one or more sets of steering (collimating) blades (or leaves) 53, 54 (discussed in more detail below). In general, a first set of collimating blades 53 may move parallel to a head-to-feet axis of the patient 22. A second set of collimating blades 53 may move transverse to the head-to-feet axis. Further the blades of each set of collimating blades 53, 54 may be moved in one direction simultaneously to steer the X-ray beam or in opposite directions to form a cone beam at one extreme or a pencil beam at the other extreme.

The detector 52 may also be conventional. The detector 52 may be structured as a fan beam detector having an arc of detector elements sufficient to span the width of the patient. The detector 52 may also be structured as an area detector adapted to detect a beam steered by the lenses 54 in the x and/or y directions shown in FIG. 1.

Under illustrated embodiments, the direction and control of X-ray transmission and detection for the collection of CT imaging data may be accomplished using one or more of a number of different methods. Under a first method, the X-ray source 50 may be provided with a linear actuator 55 adapted to move the X-ray source 50 along the length (e.g., parallel to the head-to-feet axis) of the patient 22.

The detector 52 may also be provided with a linear actuator 56 adapted to move 60 the X-ray detector 52 parallel to the head-to-feet axis of the patient 22. Both linear actuators 55, 56 may operate under control of instructions entered by the technician into the controller 14.

FIG. 2 also shows a centerline 32 perpendicular to the center axis 30. The centerline 32 defines a center position of the source 50 and detector 52 within their respective paths of travel 58, 60. Actuators 55, 56 may move the source 50 and detector 52 to locations on either side of the centerline 32.

Figure 3:
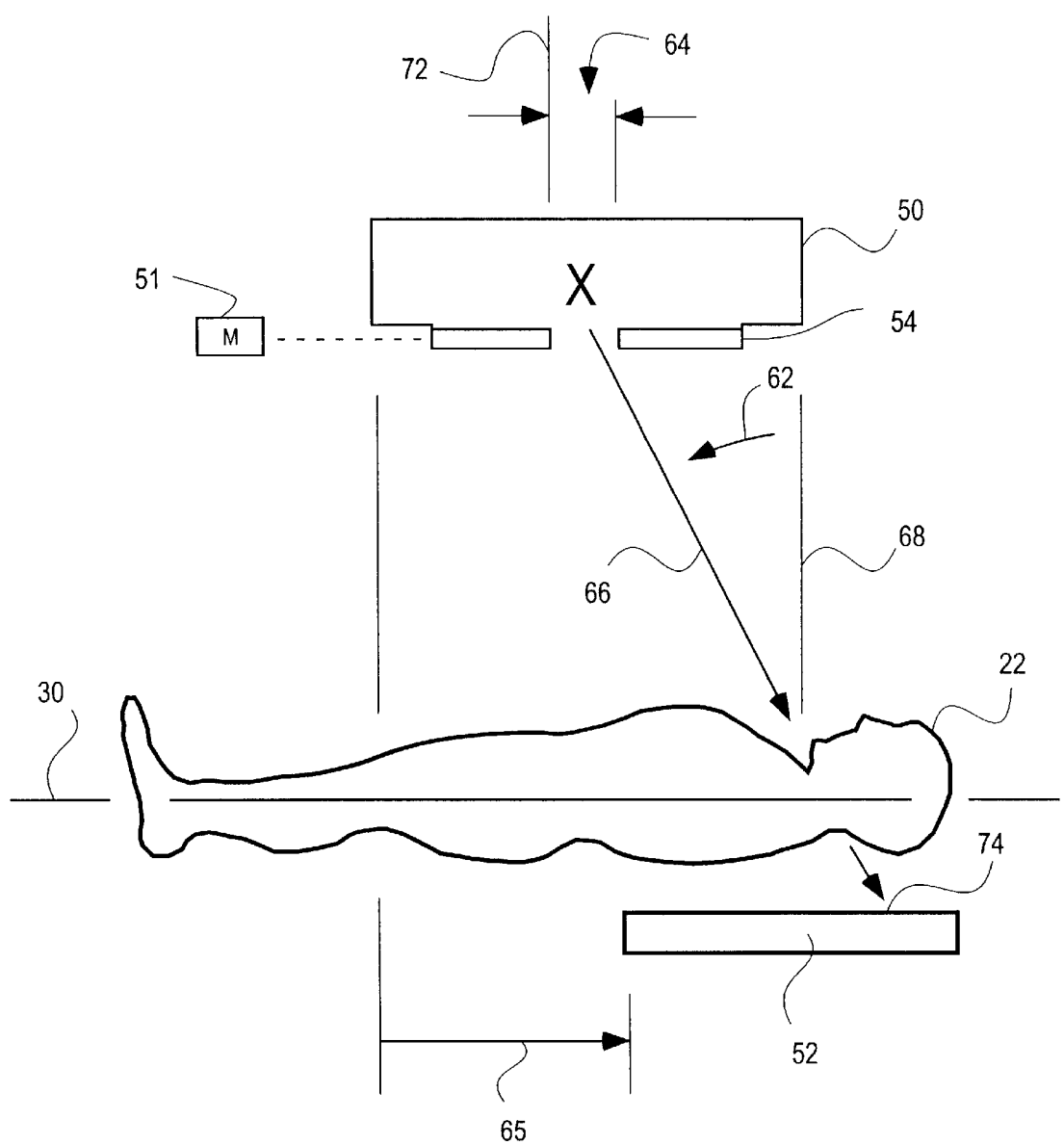
FIG. 3 depicts beam steering that may be used by the system of FIG. 1.

FIG. 3 depicts an example of a virtual tilt methodology that may be used to deliver an X-ray beam 66 to the patient 22 at an oblique angle (i.e., angularly offset from the normal to the axis 30 that passes through the head and feet of the patient 22, that is, from a line 68 that is perpendicular to the axis 30). As shown, the X-ray source 50 or detector 52 may be moved a distance 65 relative to each other to create an angle 62 between the beam 66 and the normal 68.

To achieve the offset distance 65, either the X-ray source 50 or the X-ray detector 52 may be moved. Alternatively, both the X-ray source 50 and detector 52 may be moved in opposite directions from their respective center points by an amount equal to one-half the distance 65.

To protect the patient 22 from excessive exposure to X-rays, a linear actuator (e.g., a motor) 51 coupled to the collimator 54 may move a centerline of a first set of longitudinal collimators 54 a distance 64 away from a center line 72 of the X-ray source 50. Moving the collimators 54 steers the X-rays to detectors elements 52 of the detector 52 at a terminus of the desired beam 66. The amount of shift 64 of the set of collimator blades 54 may be determined by a simple proportionality factor relating the distance of the collimator blades from the source 50 and the distance of the patient 22 and detector 52 from the source 50.

Figure 4A:
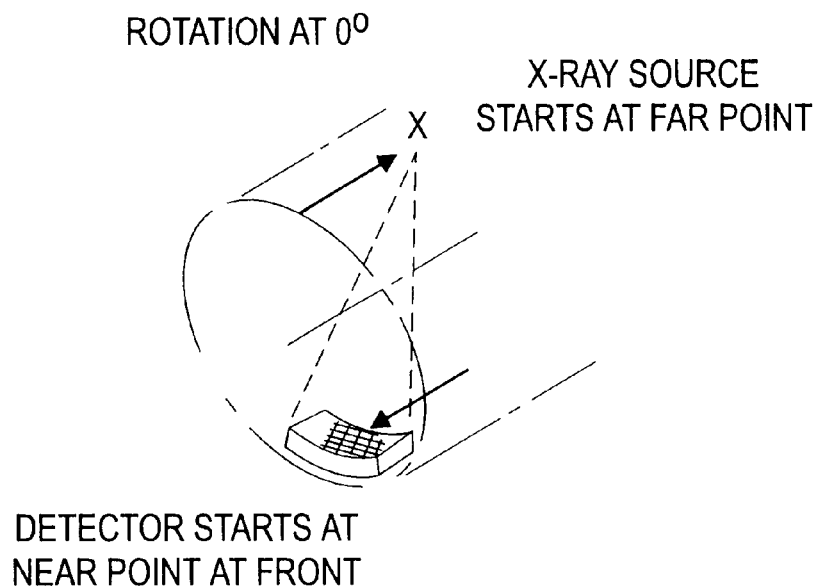
FIGS. 4a–c depicts X-ray source and detector positions under one method of use of the system of FIG. 1.
Figure 4B:
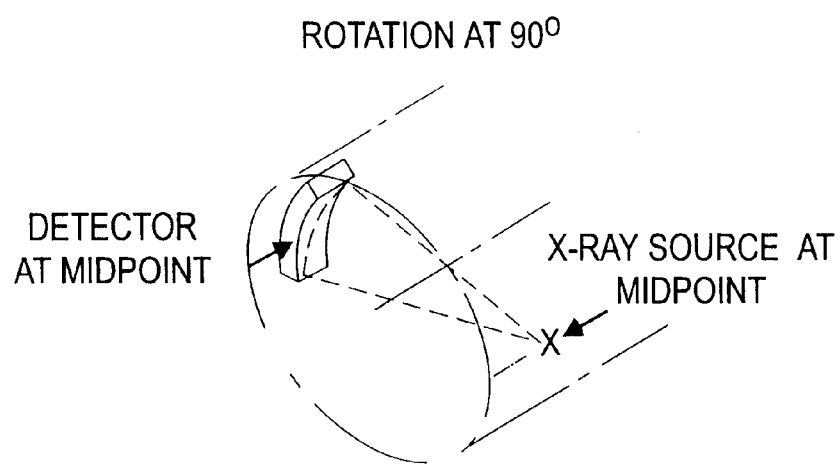
Figure 4C:
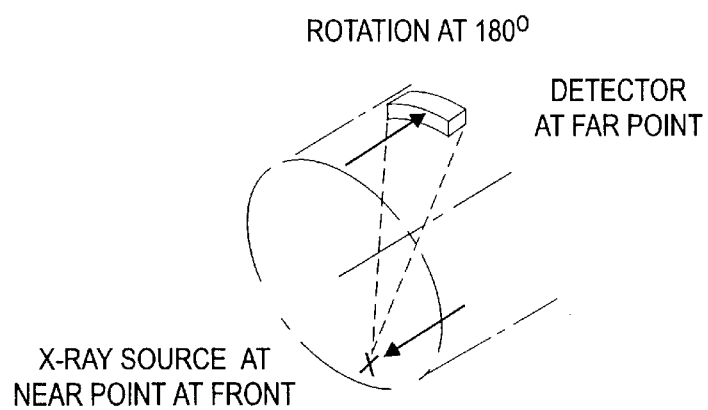

FIGS. 4a–c provides an example of how CT image data may be collected with a virtual tilt. FIGS. 4a–c show positions of the source 50 and detector 52 that provide X-ray paths that form an oblique angle with the head-to-feet axis 30. A motion control program 15 within the controller 14 may be used to define the relative positions of the source 50 and detector 52.

Figure 5A:
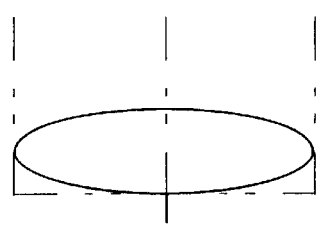
FIGS. 5a–b depicts top and side view of the CT slice that may be collected using the positions depicted in FIGS. 4a–c.
Figure 5B:
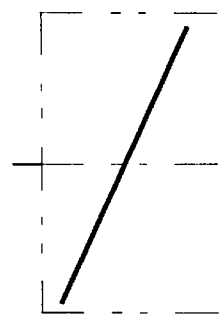
Figure 6A:
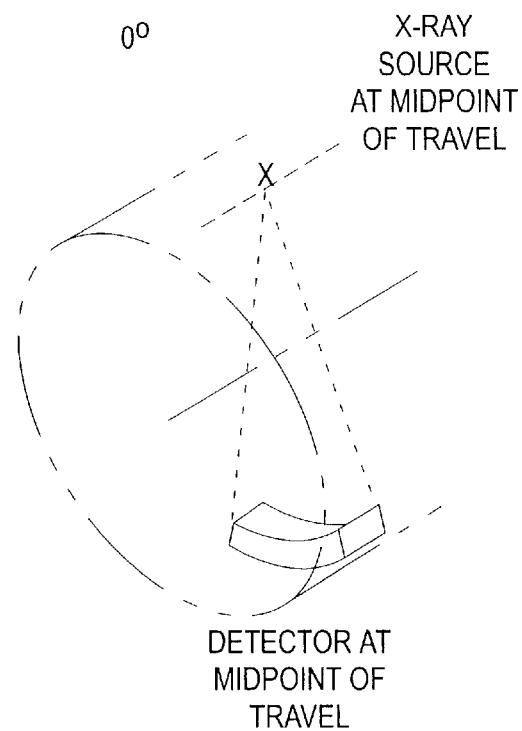
FIGS. 6a–d depicts X-ray source and detector positions under a second method of use of the system of FIG. 1.
Figure 6B:
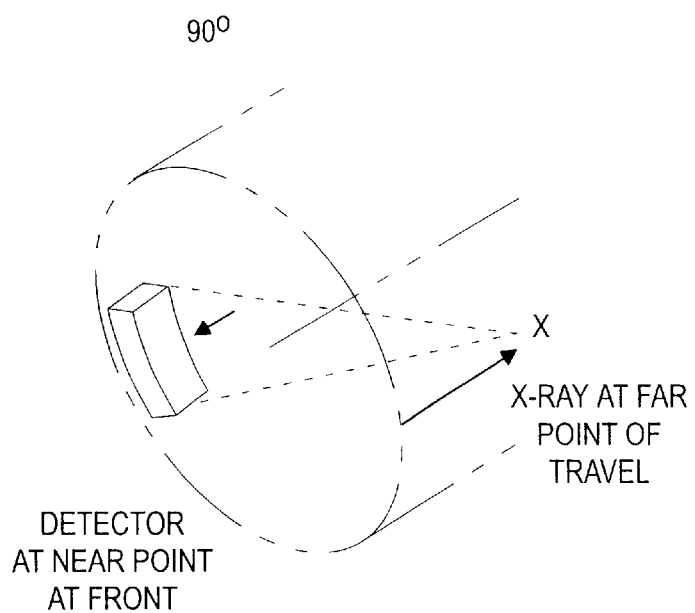
Figure 6C:
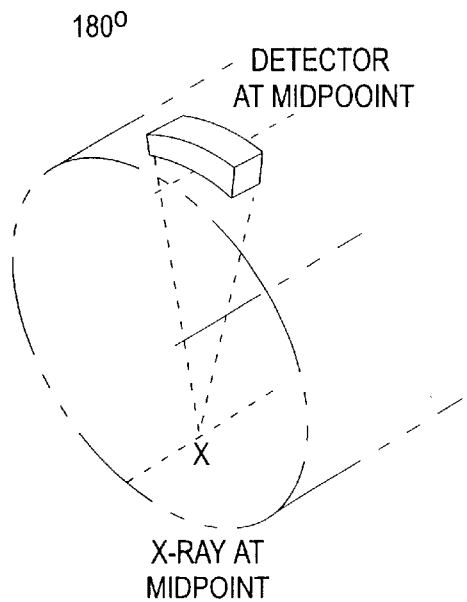
Figure 6D:
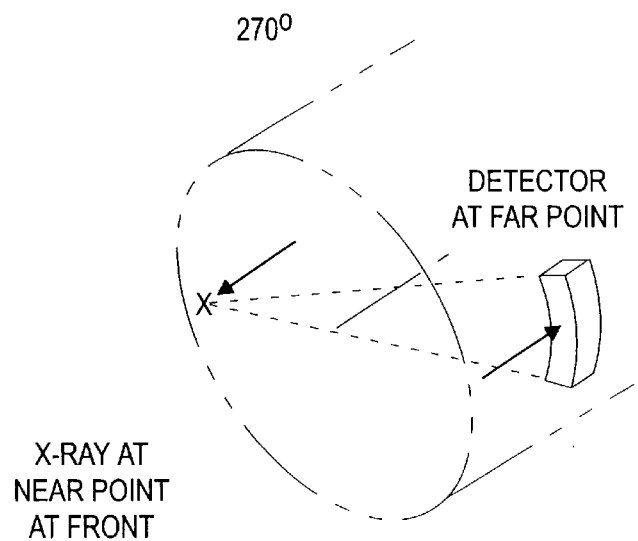

FIGS. 5a–b provides a top and side view of the slice of image data collected using the steps depicted in FIGS. 4a–c. As may be noted by comparing FIGS. 4 and 5 the movements of the source 50 and detector 52 result in movement of the X-ray path in such a way as to define a plane which is also oblique with regard to the head-to-feet axis 30.

In FIG. 4a, the scanner 24 is shown at zero degree rotation. The X-ray source 50 has been moved by the actuator 55 from the center point to a fully retracted position in preparation for scanning. In contrast, the X-ray detector 52 has been moved by the actuator 56 from the center point to a fully extended position.

As the scanner begins to rotate (e.g., clockwise) through the positions of FIGS. 4b and 4c, the actuators 55, 56 may continuously move the source 50 and detector 52 in opposite directions. At ninety degrees, the source 50 and detector 52 may be in their center positions. At one-hundred and eighty degrees, the relative axial positions of the source 50 and detector 52 may be reversed (i.e., the source 50 may be fully extended and the detector 52 fully retracted. At two-hundred and seventy degrees, the source 50 and detector 52 may again be in their center positions.

As the scanner completes a full revolution (rotates back to zero degrees), the source 50 and detector 52 may have returned to their starting positions. Once the scanner 24 has made a complete rotation, the table 22 may be incremented 26 into (or out of) a new scanning position within the scanning zone 28 and the process may be repeated. Alternatively, the table 22 may be continuously moved 26 during the rotation of the scanner 24 to capture CT image data using virtual tilt and a spiral scan.

Once CT data has been collected, two-dimensional, or (with a cone beam) three-dimensional images may be reconstructed. Any conventional method may be used (e.g., filtered backprojection, fan-beam filtered backprojection, etc.).

Figure 7A:
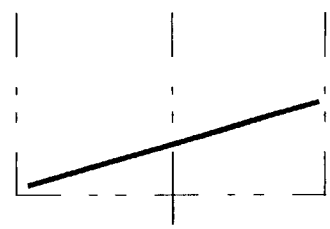
FIGS. 7a–b depicts top and side view of the CT slice that may be collected using the positions depicted in FIGS. 6a–d.
Figure 7B:
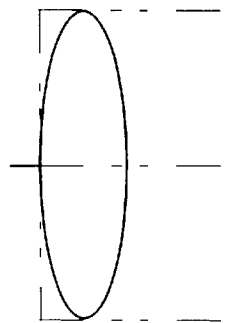

Under another embodiment, the system 10 may be used to obtain slices of the patient 22 at a horizontally oblique angle (herein referred as virtual angulation). FIGS. 7a–b show top and side views of slices that may be obtained at any horizontal angle.

FIGS. 6a–d depict positions that may be assumed by the source 50 and detector 52 during virtual angulation for one revolution of the scanner 24. FIGS. 7a–b show top and side views of a slice that may be scanned using the positions of FIGS. 6a–d. As shown, at zero degrees, the source 50 and detector 52 may reside at the midpoint. At ninety degrees, the source 50 moves to a fully retracted position, while the detector 52 moves to a fully extended position. At one-hundred and eighty degrees, the source 50 and detector 52 may again reside at the midpoint. At two-hundred and seventy degrees, the source 50 moves to a fully extended position, while the detector 52 moves to a fully retracted position.

Under another illustrated embodiment, the system 10 may be used for laminography of the patient 22. In laminography, a selected focal slice of the patient 22 may be collected that extends parallel to the axis 30. The slices may be collected using the linear actuators 54, 56 to move the source 50 and detector 52 in unison from a retracted position to an extended position (or in unison from the extended position to the retracted position) while collecting CT data along the way.

To collect each slice, the scanner 24 need not be moved, but could be. In fact, collection of slices may be accomplished through the simultaneous movement of the scanner 24 and linear actuators 54, 56.

To select a slice, the collimator blades 53, 54 may be opened sufficiently to span the selected slice. When a side-to-side rocking motion is used, the collimator blades 53, 54 may be left stationary. When the source 50 and detector 52 are moved in opposite directions, then the collimator blades 53, 45 may also be moved in opposite directions to direct energy through the selected slice 70.

Figure 8:
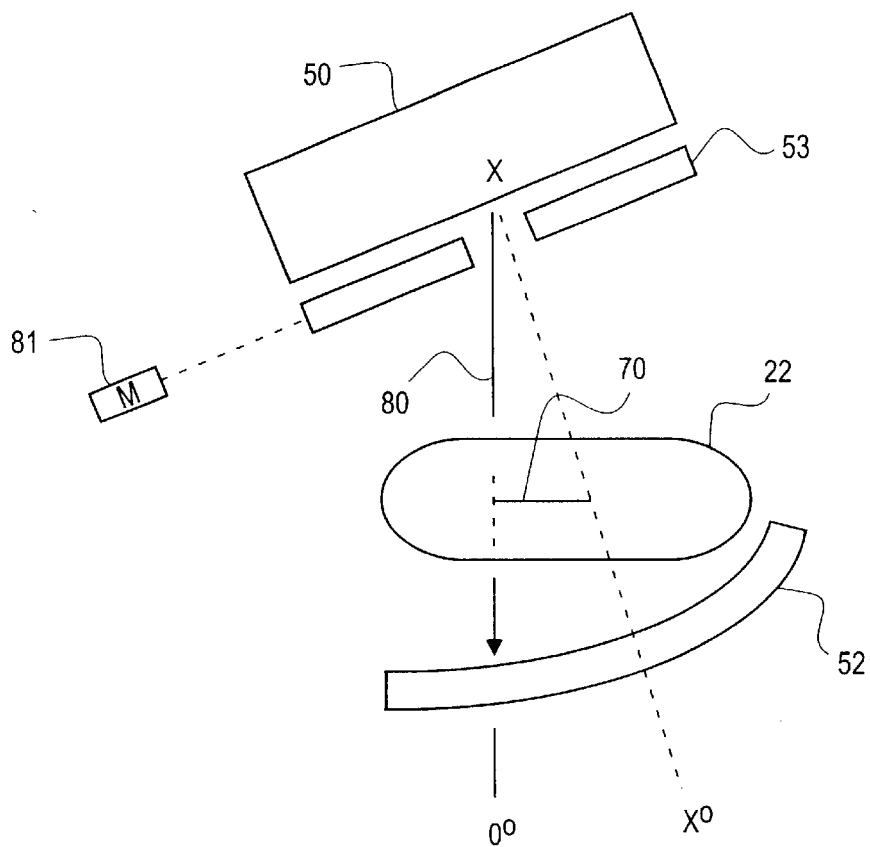
FIG. 8 depicts X-ray source, detector and collimator blade position under a third method of use of the system of FIG. 1.

FIG. 8 is an illustration of the methodology by which laminography may be performed to obtain a number of parallel slices, using a rocking motion. To select a slice 70 through the centerline axis 30 of the patient 22, the scanner 24 may rotate an equal number of degrees on either side of vertical. To select a slice on either side of the centerline axis 30, the scanner 24 may be rotated (either direction) and the first and second set of collimators 53, 54 may be adjusted to allow the focal slice 70 to remain stationary.

A similar rocking motion may be created along the head-to-feet axis of the patient 22. To allow the focal slice 70 remain stationary, both sets of collimators 53, 54 may be used to guide the beam through the appropriate regions of the patient 22.

As demonstrated by FIG. 8, the system 10 may be used to collect a longitudinal slice at any point across the patient. By adjusting the steering angle and rotation position of the scanner 24, a slice may be obtained at any orientation.

Under still another illustrated embodiment, the system 10 may be used for interventional CT imaging. Interventional CT allows medical personnel to capture and view three-dimensional images during medical procedures. The ability to capture and view images during medical procedures has great value for purposes of locating lesions or medical instruments during medical procedures.

The system 10 is particularly well suited to interventional CT because the x-ray tube and detectors project forward on short, cantilevered arms. For safety, a retractable inner cover 21 is provided for the patient and hinged covers 23 are provided for the safety of medical personnel. The covers 21, 23 may be closed during high-speed scanning, but may be opened during slow DSA, fluoroscopy laminography and, of course, interventional surgery.

In use, the protective covers 21, 23 may be closed and the patient 22 advanced into the gantry to the starting point of a fixed or helical scan. Scanning may commence. Typical speeds may range from one revolution in several seconds to two revolutions per second. Axial movement of the scan path may be achieved by movement of the source 50 and detector 52 using the linear actuators 55, 56 or by movement 26 of the patient table 20 into or out of the scanning zone 28.

A specific embodiment of a method and apparatus for collecting CT image data has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of performing computed tomography comprising the steps of:
    providing a rotating gantry for supporting an X-ray source and an X-ray detector, and for rotating the X-ray source and X-ray detector completely around a head-to-feet axis of a prone patient;
    moving one of the X-ray source and the X-ray detector parallel to the head-to-feet axis of the prone patient; and
    collecting tomographic data from the X-ray detector as the one of the X-ray source and X-ray detector moves along the head-to-feet axis of the prone patient and the rotating gantry rotates the X-ray source and the X-ray detector completely around the head-to-feet axis of the prone patient.

2. The method of performing computed tomography as in claim 1 further comprising moving both the X-ray source and X-ray detector parallel to the head-to-feet axis.

3. The method of performing computed tomography as in claim 2 further comprising moving the X-ray source and X-ray detector in opposite directions.

4. The method of performing computed tomography as in claim 1 further comprising rotating the X-ray source and detector around the head-to-feet axis.

5. The method of performing computed tomography as in claim 1 further comprising steering X-rays from the X-ray source into the X-ray detector during movement of the X-ray detector along the head-to-feet axis.

6. The method of performing computed tomography as in claim 5 wherein the step of steering further comprises moving a set of collimator blades parallel to the head-to-feet axis of the prone patient.

7. The method of performing computed tomography as in claim 4 wherein the step of steering further comprises moving a set of collimator blades transverse to the head-to-feet axis of the prone patient.

8. The method of performing computed tomography as in claim 1 further comprising transmitting X-rays along an X-ray path forming an oblique angle with the head-to-feet axis.

9. The method of performing computed tomography as in claim 8 further comprising moving the X-ray path to define a data collection slice forming an oblique angle with the head-to-feet axis.

10. The method of performing computed tomography as in claim 1 further comprising moving the X-ray source and X-ray detector to form a data collection slice parallel to the head-to-feet axis.

11. An apparatus for performing computed tomography comprising:
    means for moving one of an X-ray source and an X-ray detector parallel to a head-to-feet axis of a prone patient;
    means for rotating the X-ray source and the X-ray detector completely around the head-to-feet axis of the prone patient; and
    means for collecting tomographic data from the X-ray detector as the one of the X-ray source and X-ray detector moves along the head-to-feet axis of the prone patient and the means for rotating rotates the X-ray source and the X-ray detector completely around the head-to-feet axis of the prone patient.

12. The apparatus for performing computed tomography as in claim 11 further comprising means for moving both the X-ray source and X-ray detector parallel to the head-to-feet axis.

13. The apparatus for performing computed tomography as in claim 12 further comprising means for moving the X-ray source and X-ray detector in opposite directions.

14. The apparatus for performing computed tomography as in claim 11 further comprising means for rotating the X-ray source and detector around the head-to-feet axis.

15. The apparatus for performing computed tomography as in claim 11 further comprising means for steering X-rays from the X-ray source into the X-ray detector during movement of the X-ray detector along the head-to-feet axis.

16. The apparatus for performing computed tomography as in claim 15 wherein the means for steering further comprises means for moving a set of collimator blades parallel to the head-to-feet axis of the prone patient.

17. The apparatus for performing computed tomography as in claim 14 wherein the means for steering further comprises means for moving a set of collimator blades transverse to the head-to-feet axis of the prone patient.

18. The apparatus for performing computed tomography as in claim 11 further comprising means for transmitting X-rays along an X-ray path forming an oblique angle with the head-to-feet axis.

19. The apparatus for performing computed tomography as in claim 18 further comprising means for moving the X-ray path to define a data collection slice forming an oblique angle with the head-to-feet axis.

20. The apparatus for performing computed tomography as in claim 11 further comprising means for moving the X-ray source and X-ray detector to form a data collection slice parallel to the head-to-feet axis.

21. An apparatus for performing computed tomography comprising:
   an X-ray source;
   an X-ray detector;
   a first linear actuator adapted to move one of an X-ray source and an X-ray detector parallel to a head-to-feet axis of a prone patient;
   a gantry adapted to rotate the X-ray source and the X-ray detector completely around the head-to-feet axis of the prone patent; and
   a controller adapted to collect tomographic data from the X-ray detector as the one of the X-ray source and X-ray detector moves along the head-to-feet axis of the prone patient and the gantry rotates the X-ray source and the X-ray detector completely around the head-to-feet axis of the prone patient.

22. The apparatus for performing computed tomography as in claim 21 further comprising a second linear actuated adapted to move both the X-ray source and X-ray detector parallel to the head-to-feet axis.

23. The apparatus for performing computed tomography as in claim 21 further comprising a gantry adapted to rotate the X-ray source and detector around the head-to-feet axis.

24. The apparatus for performing computed tomography as in claim 21 further comprising a collimator adapted to steer X-rays from the X-ray source into the X-ray detector during movement of the X-ray detector along the head-to-feet axis.

25. The apparatus for performing computed tomography as in claim 24 wherein the collimator further comprises a collimator actuator adapted to move a set of collimator blades parallel to the head-to-feet axis of the prone patient.

26. The apparatus for performing computed tomography as in claim 21 further comprising a motion control program adapted to transmit X-rays along an X-ray path forming an oblique angle with the head-to-feet axis.

27. A method of performing computed tomography comprising the steps of:
   moving an X-ray source in a first direction parallel to a head-to-feet axis of a prone patient;
   moving an X-ray detector in a second direction opposite the first direction parallel to the head-to-feet axis of the prone patient;
   moving the X-ray source and the X-ray detector completely around the head-to-feet axis; and
   collecting tomographic data from the X-ray detector as the X-ray source and X-ray detector move along the head-to-feet axis of the prone patient and the X-ray source and X-ray detector move completely around the head-to-feet axis of the prone patient.

28. The method of performing computed tomography as in claim 27 further comprising moving the X-ray source and X-ray detector in opposite directions.

29. The method of performing computed tomography as in claim 27 further comprising rotating the X-ray source and detector around the head-to-feet axis.

30. The method of performing computed tomography as in claim 27 further comprising steering X-rays from the X-ray source into the X-ray detector during movement of the X-ray source and X-ray detector.

31. The method of performing computed tomography as in claim 27 wherein the step of steering further comprises moving a set of collimator blades parallel to the head-to-feet axis of the prone patient.

32. The method of performing computed tomography as in claim 27 wherein the step of steering further comprises moving a set of collimator blades transverse to the head-to-feet axis of the prone patient.

* * * * *